United States Patent [19]

Weiner

[11] Patent Number: 4,659,173
[45] Date of Patent: Apr. 21, 1987

[54] MICROTOMY SPECIMEN BLOCK HAVING A FIBER OPTIC TRANSMISSION MEDIUM THEREIN AND METHOD OF FORMING THE SAME

[75] Inventor: Allan J. Weiner, Westport, Conn.

[73] Assignee: RMC, Inc., Tucson, Ariz.

[21] Appl. No.: 561,524

[22] Filed: Dec. 15, 1983

[51] Int. Cl.⁴ .................................................. G02B 5/14
[52] U.S. Cl. .............................. 350/96.24; 350/96.10; 350/96.20; 249/187 R; 362/32
[58] Field of Search ............... 350/96.10, 96.20, 96.24; 362/32; 264/1.5; 249/82, 83, 187 R

[56] References Cited

U.S. PATENT DOCUMENTS

| 2,996,762 | 8/1961 | McCormick | 18/26 |
| 3,103,844 | 9/1963 | Persson | 83/167 |
| 3,619,594 | 11/1971 | Morez | 362/32 |
| 3,621,752 | 11/1971 | Sitte | 90/11 R |
| 3,828,641 | 8/1974 | Sitte | 83/703 |
| 4,272,049 | 6/1981 | Kindel | 249/83 |
| 4,286,839 | 9/1981 | Ilzig et al. | 350/96.24 |
| 4,292,260 | 9/1981 | Cheung | 264/1.5 |
| 4,531,702 | 7/1985 | Plummer | 264/1.5 X |

Primary Examiner—William L. Sikes
Assistant Examiner—Akm E. Ullah

[57] ABSTRACT

An apparatus for backlighting a microtomy specimen that includes a fiber optic transmission medium arranged in a light transmissive relationship with a source of illumination.

8 Claims, 9 Drawing Figures

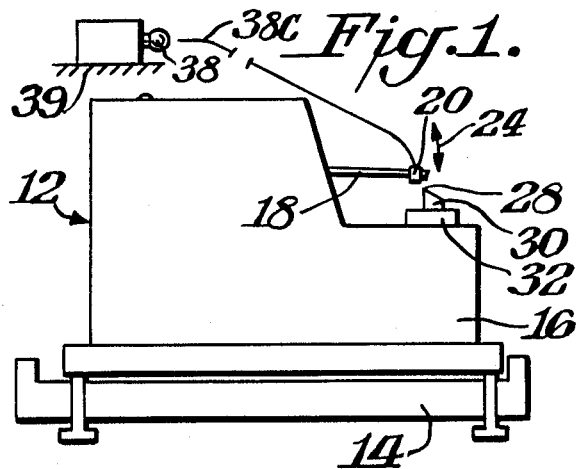
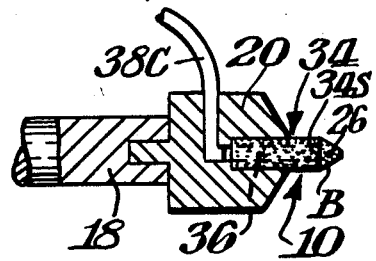
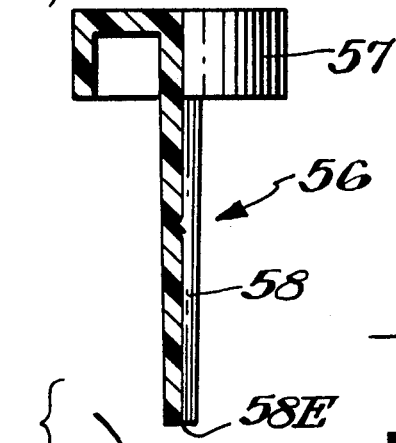
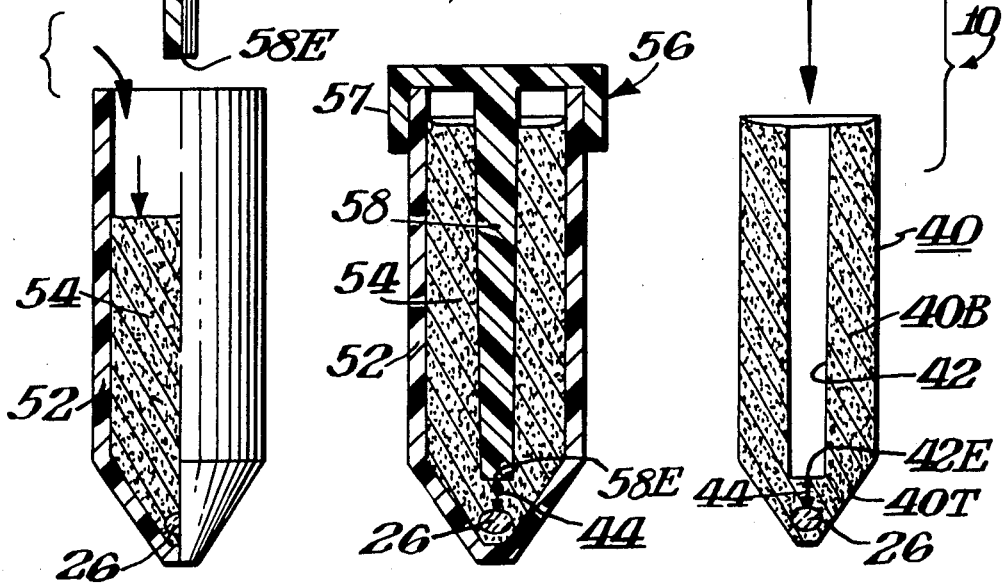

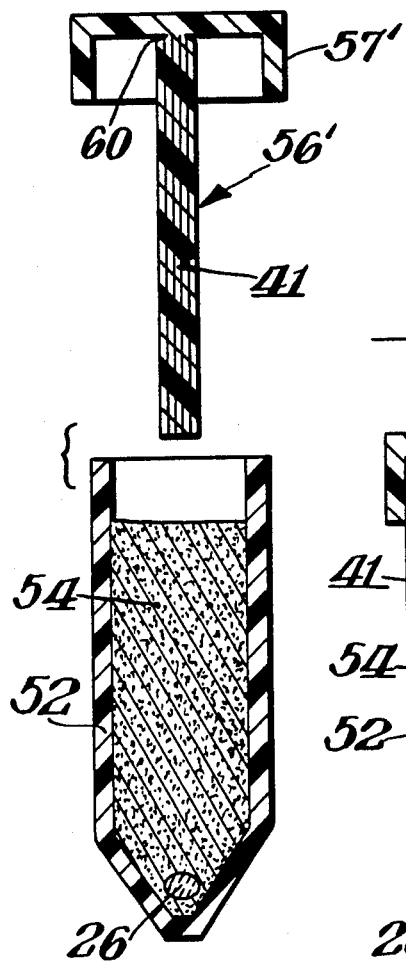
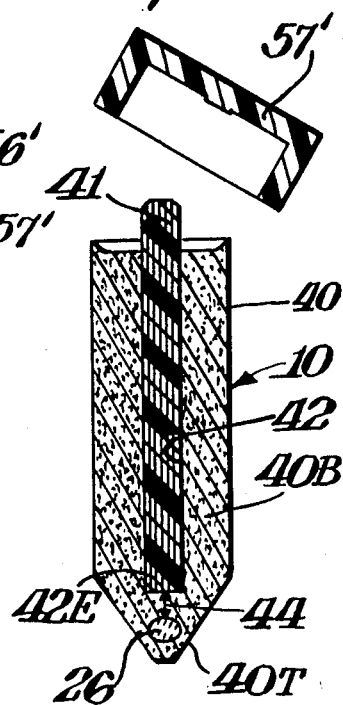
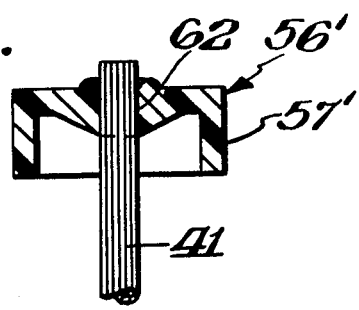

MICROTOMY SPECIMEN BLOCK HAVING A FIBER OPTIC TRANSMISSION MEDIUM THEREIN AND METHOD OF FORMING THE SAME

BACKGROUND OF THE INVENTION

1. Field of the Invention

This invention relates to an apparatus for backlighting a microtomy specimen.

2. Description of the Prior Art

When it is desired to slice thin or very thin sections of a specimen that specimen is embedded within a mass of embedding medium to form a specimen block. Typically, the block takes either a substantially cylindrical or a rectangular flattened form. The specimen block, however configured, is mounted by a specimen holder carried at the outboard end of a pivotally movable cutting arm of a microtome. Pivotal movement of the microtome arm followed by an axial advance thereof moves the specimen block with respect to a cutting blade and results in the production of thin or very thin sections of the specimen.

In order to assist the microtome operator during the cutting of the sections it is desirable to illuminate the specimen embedded within the block from the rear thereof. A commercially available microtome instrument manufactured and sold by C. Reichert Optische Werke, A.G., as the "Ultracut" accomplishes this purpose by the provision of a lamp bulb in a recess formed in the specimen arm immediately behind the specimen block. Light from the lamp backlights the specimen, thereby assisting the operator during the cutting of the same.

However, since the source of illumination in the commercially available instrument is separated from the specimen by the body of the specimen block the full advantage potentially afforded by the backlighting of the specimen is not attained. Additionally, the source is close enough to the block to act as a heat source which could potentially adversely affect the specimen block.

Accordingly, in view of the foregoing, it is believed desirable to provide an arrangement for mounting a specimen block to a microtome which more efficiently backlights the specimen. It is believed to be further advantageous to provide a specimen block which is adapted to utilize fiber optic media in order to transmit light to backlight the specimen. Such an arrangement has the beneficial result of permitting the source of illumination to be removed to a point remote from the specimen block, thereby avoiding any potential adverse effects due to heating of the specimen.

SUMMARY OF THE INVENTION

The invention relates generally to an apparatus which uses a fiber optic transmission medium for backlighting a specimen for microtomy. By use of a fiber optic medium the source of illumination may be remotely disposed with respect to specimen and yet, simultaneously, light may be transmitted to effectively backlight the specimen.

In accordance with one aspect of the invention the apparatus includes a plug sized for receipt by the microtome arm in a light transmissive relationship with a source of illumination. A portion of the plug is formed from a fiber optic transmission medium. The plug has a specimen mounting surface thereon adapted to receive and to support a microtomy specimen block.

In another aspect the apparatus takes the form of a specimen block of either a cylindrical or flat form carrying a fiber optic transmission cable therein. The cable is arranged to terminate a predetermined close distance immediately adjacent to the specimen to be sectioned. According to the present invention, the apparatus is formed by first disposing within a suitable mold or capsule a specimen of the material to be sectioned, and thereafter, embedding the same within a mass of embedding medium. An elongated member of a predetermined length is inserted into the still-molten embedding material such that the distal end of the elongated portion lies within a predetermined close distance of and in spaced adjacency to the specimen. A fiber optic cable is thereafter mounted in the bore so formed. The cap and elongated member are integral and may be withdrawn while or after the embedding medium sets in order to define an access bore. Alternatively, in fabricating the apparatus an insert having an elongated fiber optics light cable may be used as the elongated member inserted into the embedding medium. In this instance, the elongated cable is detachably connected to the cap such that the cap may be removed from the end leaving the cable projected from the rear of the apparatus.

BRIEF DESCRIPTION OF THE DRAWINGS

The invention may be more fully understood from the following detailed description, taken in connection with the accompanying drawings which form a part of this application and in which:

FIG. 1 is a highly stylized pictorial representation of a microtome instrument which utilizes an apparatus for backlighting specimen for microtomy in accordance with the present invention;

FIG. 2 is an enlarged view of the outboard end of the cutting arm of the microtome instrument of FIG. 1 having thereon an apparatus in accordance with one aspect of the present invention;

FIGS. 3 through 5 and 6 through 8 are, respectively, a series of stylized schematic representations of the method steps by which an apparatus embodying alternate aspects of the present invention may be fabricated; and FIG. 9 is an enlarged view of a cap used in accordance with one aspect of the present invention.

DETAILED DESCRIPTION OF THE INVENTION

Throughout the following detailed description similar reference numerals refer to similar elements in all Figures of the drawings.

Reference to FIG. 1 shown as a highly stylized pictorial representation of a microtome instrument which utilizes an apparatus for backlighting a specimen for microtomy in accordance with this invention. The apparatus is generally indicated by reference character 10 and carries a fiber optic transmission medium therein.

The microtome instrument generally indicated by reference character 12 includes a framework 14 securely supporting the instrument on a suitable workbench or a table. Mounted to the frame is superstructure 16 to which a microtome arm 18 is pivotally mounted by means of appropriate bearings as will be appreciated by those with skill in the art.

The outward end of the microtome arm 18 carries a specimen holder 20. The specimen holder 20 is arranged to receive the apparatus 10 in accordance with the present invention. The microtome arm is advancable axially with respect thereto by a suitable advance mechanism (not shown). A microtome drive (not shown) serves to reciprocally displace the microtome arm in a vertical plane in the direction of arrows 24. The combination of the reciprocal motion of the microtome arm coupled with the axial advance thereof serves to sequentially bring a specimen 26 carried by the apparatus 10 over the cutting edge 28 of a microtome knife 30 secured by a stage 32 to the superstructure 16.

In accordance with one aspect of the present invention, as best shown in FIG. 2, the apparatus 10 carried by specimen arm 18 takes the form of a plug 34 sized for receipt by the holder 20. The plug 34 has a specimen support surface 34S upon which a specimen block B may be mounted. Any suitable means may be used to mount the block B to the support surface 34S of the plug 34. At least a portion of the plug 34 is formed of a fiber optic transmission medium, such as a cable 36. The cable 36 is arranged to lie in a light transmissive relationship with a suitable light source 38. The source 38 is mounted on a suitable support surface 39 at any convenient location remote from the specimen 26. The source 38 is connected to the plug 34 in a light transmissive connection via a fiber optic cable 38C.

The apparatus 10 may alternately take the form of a modified specimen block indicated in the drawings by reference character 40. The block 40 may be formed as either a cylindrical or flat embedment. The block 40 has a body 40B and a tapered end portion 40T. Embedded within and at the apex of the end portion 40T is the specimen 26 of material to be sectioned by the microtome instrument 12.

In accordance with each alternate aspect of the invention shown in FIGS. 5 and 8 the apparatus 10 carries a fiber optic cable 41 therein. In accordance with one method of manufacturing such an apparatus 10 a bore 42 is provided within and through the body 40B of the specimen block 40. The inner end 42E of the bore 42 is arranged to terminate within a predetermined close distance 44 of and adjacent to the embedded specimen 26. The cable 41 is then inserted into the block. In accordance with another method of manufacturing such an apparatus 10, the specimen block 40 is formed with the fiber optic cable 41 embedded therein. The cable 41 may, in practice, be configured from one or from a bundle of optical fibers.

With references to FIGS. 3 through 5, shown is the diagrammatic sequence of the first method used to fabricate the apparatus 10 in accordance with the invention. In the first step (FIG. 3), a specimen 26 to be sectioned is disposed in any convenient location within a capsule or mold 52 in either cylindrical or flat embedment form. Therefore a mass 54 of embedding medium is introduced into the capsule 52 so as to completely surround the specimen 26 and extend rearwardly therefrom a predetermined operating distance consistent with well known principles in the art. Any suitable epoxy based embedding material may be used.

As shown in FIGS. 3 and 4, an insert 56 including a cap 57 having an elongated projection 58 thereon is inserted into the mass 54 of embedding material such that the distal end 58E of the elongated member 58 is disposed within the predetermined close distance 44 of the specimen 26. After allowing a suitable period in which to permit the embedding medium to set up to a semi-rigid condition, the insert 56 with the elongated member 58 thereon are removed from the mold 52. This action serves to define the bore 42 extending through the specimen block 40. It may be necessary in some instances to coat the elongated member 58 with a suitable release agent in order to facilitate the extraction thereof from the semi-rigid mass of embedding medium. In some instances, the cap 57 may be omitted and the elongated member 58 itself inserted into the mass 54 of embedding medium. Thereafter, the cable 41 is introduced into the bore 42, completing the apparatus 10.

In the alternate method, as depicted in FIGS. 6 through 8, the elongated projection of the insert 56' may itself take the form of a fiber optics light cable 41 detachably mounted to the cap 57'. In this event, after insertion of the cable 41 into the mass 54 of embedding material the cap 57' is detached from the cable 41 leaving the same in place within the body 40B of the specimen block. It is to be understood that any suitable means of detachable attachment for the cable 41 to the cap 57' may be utilized. For example, the cable 41 may be notched, as at 60, or the cable 41 may be press fit, as at 62 (FIG. 9) to the cap 57.

It should be understood that the fiber optic cable 41 may extend through the body 40B of the specimen block 40 so as to terminate sidewise with respect to the specimen. In addition, of course, more than one cable may be detachably secured to the undersurface of the cap thereby permitting illumination of the specimen 26 from more than one direction.

In operation, the apparatus 10 in accordance with the present invention is mounted on the specimen holder 20 such that the cable 41 disposed therein registers with the light source 38 in a light transmissive arrangement. Accordingly, specimen 26 is adequately backlit.

Those skilled in the art having benefit of the foregoing teachings of the present invention as set forth hereinabove, may effect numerous modifications thereto. It is to be understood, however, that such modifications lie within the scope of the present invention as defined by the appended claims.

What is claimed is:

1. A method of fabricating an apparatus for backlighting a specimen for use in a microtome instrument comprising the steps of:
   (a) disposing a specimen to be sectioned in a mold;
   (b) introducing an embedding medium into the mold around the specimen; and
   (c) inserting an elongated member having a proximal and distal end thereon into the embedding medium such that the distal end of the elongated member lies within a predetermined close distance of the specimen.

2. The method according to claim 1 further comprising the steps of:
   (d) removing the elongated member from the embedding medium after the embedding medium begins to set-up to define a bore within the specimen block; and
   (e) inserting a fiber optic transmissive member having an end thereon into the bore such that the end of the fiber optic transmission member lies within the predetermined close distance of the specimen.

3. The method of claim 1 wherein the elongated member is formed of a fiber optic transmissive medium attached to a cap, further comprising the step of: (d) detaching the cap from the elongated member such that the elongated member remains within the embedding medium.

4. The apparatus formed by the process of claim 2.

5. The apparatus formed by the process of claim 3.

6. Apparatus for backlighting a specimen for use in a microtome comprising a plug sized for receipt by the specimen arm of the microtome in a light transmissive relationship with a source of illumination, a portion of the plug being formed of a fiber optic transmission medium, the plug having a specimen block mounting surface adapted to receive and support a microtomy specimen block thereon.

7. Apparatus for backlighting a microtomy specimen comprising a body of embedding material having a specimen to be sectioned embedded therein and a fiber optic cable having an end thereon embedded within the specimen block, the end of the cable terminating within a predetermined close distance of the specimen.

8. A molding insert useful for fabricating an apparatus for backlighting a microtomy specimen comprising a cap and an elongated fiber optic cable detachably secured to the cap.

* * * * *